United States Patent
Carter et al.

(10) Patent No.: US 11,069,440 B2
(45) Date of Patent: Jul. 20, 2021

(54) APPLICATION FOR MEASURING MEDICAL SERVICE PROVIDER WAIT TIME

(71) Applicants: Eric Carter, Tarpon Springs, FL (US); Kevin Makati, Tampa, FL (US); Brandon Sultemeier, Austin, TX (US)

(72) Inventors: Eric Carter, Tarpon Springs, FL (US); Kevin Makati, Tampa, FL (US); Brandon Sultemeier, Austin, TX (US)

(73) Assignee: FAST PATHWAY, INC., Tampa, FL (US)

(*) Notice: Subject to any disclaimer, the term of this patent is extended or adjusted under 35 U.S.C. 154(b) by 408 days.

(21) Appl. No.: 16/264,256

(22) Filed: Jan. 31, 2019

(65) Prior Publication Data

US 2019/0237187 A1 Aug. 1, 2019

Related U.S. Application Data

(60) Provisional application No. 62/624,293, filed on Jan. 31, 2018.

(51) Int. Cl.
*G16H 40/20* (2018.01)
*H04L 29/08* (2006.01)
(Continued)

(52) U.S. Cl.
CPC ......... *G16H 40/20* (2018.01); *G06Q 30/0282* (2013.01); *H04L 67/18* (2013.01); *H04W 4/021* (2013.01)

(58) Field of Classification Search
CPC .......... G06Q 10/1091; G06Q 30/0282; G16H 40/20; H04L 67/18; H04W 4/021
See application file for complete search history.

(56) References Cited

U.S. PATENT DOCUMENTS

| 8,000,979 B2 | 8/2011 | Blom |
| 8,484,048 B2 | 7/2013 | Halsted et al. |

(Continued)

FOREIGN PATENT DOCUMENTS

WO 20110140290 A1 11/2011

OTHER PUBLICATIONS

Garzon et al., "Gefencing 2.0:Taking Location-based Notifications to the Next Level", UBICOMP, Sep. 2014, ACM publishing, 12 pages total.*

(Continued)

*Primary Examiner* — Todd L Barker
(74) *Attorney, Agent, or Firm* — Michael D. Marra; Shumaker, Loop & Kendrick, LLP

(57) ABSTRACT

A mobile device application for measuring actual wait times experienced by patients of doctors or other medical service providers. A patient launches the application on the mobile device, views available service providers and selects a provider. The patient starts the clock for the selected service provider when the wait begins, and stops the clock when the wait ends. At this time or after the visit, the patient can post their actual wait time, a star-based rating and comments for other patients to view on the application or on a web page equivalent. The patient must be within a GPS-verified geofence around the provider's office in order for the wait time to be considered valid. An integrated real-time messaging application used during surgical procedures is also disclosed.

18 Claims, 13 Drawing Sheets

(51) Int. Cl.
  *H04W 4/021*  (2018.01)
  *G06Q 30/02*  (2012.01)

(56) References Cited

U.S. PATENT DOCUMENTS

| | | | | |
|---|---|---|---|---|
| 9,961,507 | B1* | 5/2018 | Mendelson | H04W 48/10 |
| 10,762,473 | B2* | 9/2020 | Porter | G06Q 10/1091 |
| 2007/0226008 | A1 | 9/2007 | Halsted et al. | |
| 2012/0130730 | A1 | 5/2012 | Setlur et al. | |
| 2012/0172027 | A1* | 7/2012 | Partheesh | H04M 1/72415 455/420 |
| 2013/0144637 | A1* | 6/2013 | Bertha | G16H 80/00 705/2 |
| 2015/0081348 | A1 | 3/2015 | Avera et al. | |
| 2015/0081487 | A1* | 3/2015 | Porter | G06Q 10/1091 705/32 |
| 2015/0088671 | A1 | 3/2015 | Xiong et al. | |
| 2015/0213414 | A1 | 7/2015 | Zuckerman et al. | |
| 2016/0253464 | A1* | 9/2016 | Balwani | G06Q 10/00 705/2 |
| 2016/0364547 | A1* | 12/2016 | Love | G16H 20/10 |
| 2017/0046490 | A1 | 2/2017 | Bollwinkel | |
| 2017/0118590 | A1* | 4/2017 | Baca | H04W 4/029 |
| 2018/0052958 | A1* | 2/2018 | Crawford | G06F 21/6245 |
| 2018/0130554 | A1* | 5/2018 | Cheng | G16H 40/20 |
| 2018/0232704 | A1* | 8/2018 | Porter | G06Q 10/1091 |
| 2018/0295471 | A1* | 10/2018 | Dewan | H04W 4/025 |
| 2019/0121943 | A1* | 4/2019 | Wong | H04L 63/101 |
| 2021/0020307 | A1* | 1/2021 | Bhimavarapu | G16H 40/40 |

OTHER PUBLICATIONS

Karimi et al., "SoNavNet" A Framework for Social Navigation Networks, Nov. 2009, ACM pulbilishing, 7 pages total.*
https://jellyfishhealth.com/jellyfish-health-news/Jellyfish-health-launches-mobile-app-to-reduce-patient-wait-times, Nov. 25, 2017; 5 pages.
https://www.ahcmedia.com/articles/137113-app-lets-patients-check-urgent-wait-times-before-leaving-home; Jan. 20, 2017; 10 pages.
https://www.mobihealthnews.com/content/cvs-minuteclinic-app-get-new-wait-times-remote-scheduling-features; Comstock, Jonah; Dec. 10, 2015; 14 pages.

* cited by examiner

US 11,069,440 B2

APPLICATION FOR MEASURING MEDICAL SERVICE PROVIDER WAIT TIME

CROSS-REFERENCE TO RELATED APPLICATIONS

This application claims the benefit of the priority date of U.S. Provisional Patent Application Ser. No. 62/624,293, titled APPLICATION FOR MEASURING MEDICAL SERVICE PROVIDER WAIT TIME, filed Jan. 31, 2018.

BACKGROUND

Field

This present disclosure relates generally to the field of GPS-enabled mobile device applications and, more particularly, to a mobile device application which allows a patient to measure their actual wait time to see a doctor or other medical service provider and post the wait time and a rating for other patients to view, where the patient must be within a GPS-verified geofence around the doctor's office in order for the wait time to be considered valid.

Discussion

Doctors and other health care service providers are typically very busy. Emergency rooms (ERs) obviously cannot predict in advance the volume of patients that they will see on any given day, nor the complexity of the cases, and it is therefore possible for back-ups to occur. But even non-ER doctors and other medical service providers who work on an appointment schedule can be overwhelmed by a combination of unscheduled walk-in patients, late arriving patients, appointment overruns, staff shortages and other factors.

When the factors mentioned above occur, their combined effect can cause patient wait times to increase dramatically—even for patients having an appointment. Most people find it very frustrating to endure lengthy wait times, and as a result, service providers have attempted to reduce wait times or at least communicate them to prospective patients. Mobile device applications have been developed to allow patients to view ER and doctor's office wait times, schedule appointments, and receive other information. However, the wait times reported in these existing applications is estimated or otherwise determined by the service provider, and may or may not reflect the actual experience of the patients.

SUMMARY

The present disclosure describes a mobile device application for measuring and reporting actual wait times experienced by patients of doctors or other medical service providers. A patient launches the application on the mobile device, views available service providers and selects a provider. In the application, the patient starts a clock for the selected service provider when the wait begins, and stops the clock when the wait ends. At this time or after the visit, the patient can post their actual wait time, a star-based rating and comments for other patients to view on the application or on a web page equivalent. The patient must be within a GPS-verified geofence around the provider's office in order for the wait time to be considered valid. An integrated real-time messaging application used during surgical procedures is also disclosed.

Additional features of the presently disclosed methods will become apparent from the following description and appended claims, taken in conjunction with the accompanying drawings.

DETAILED DESCRIPTION OF THE EMBODIMENTS

Figure 1:
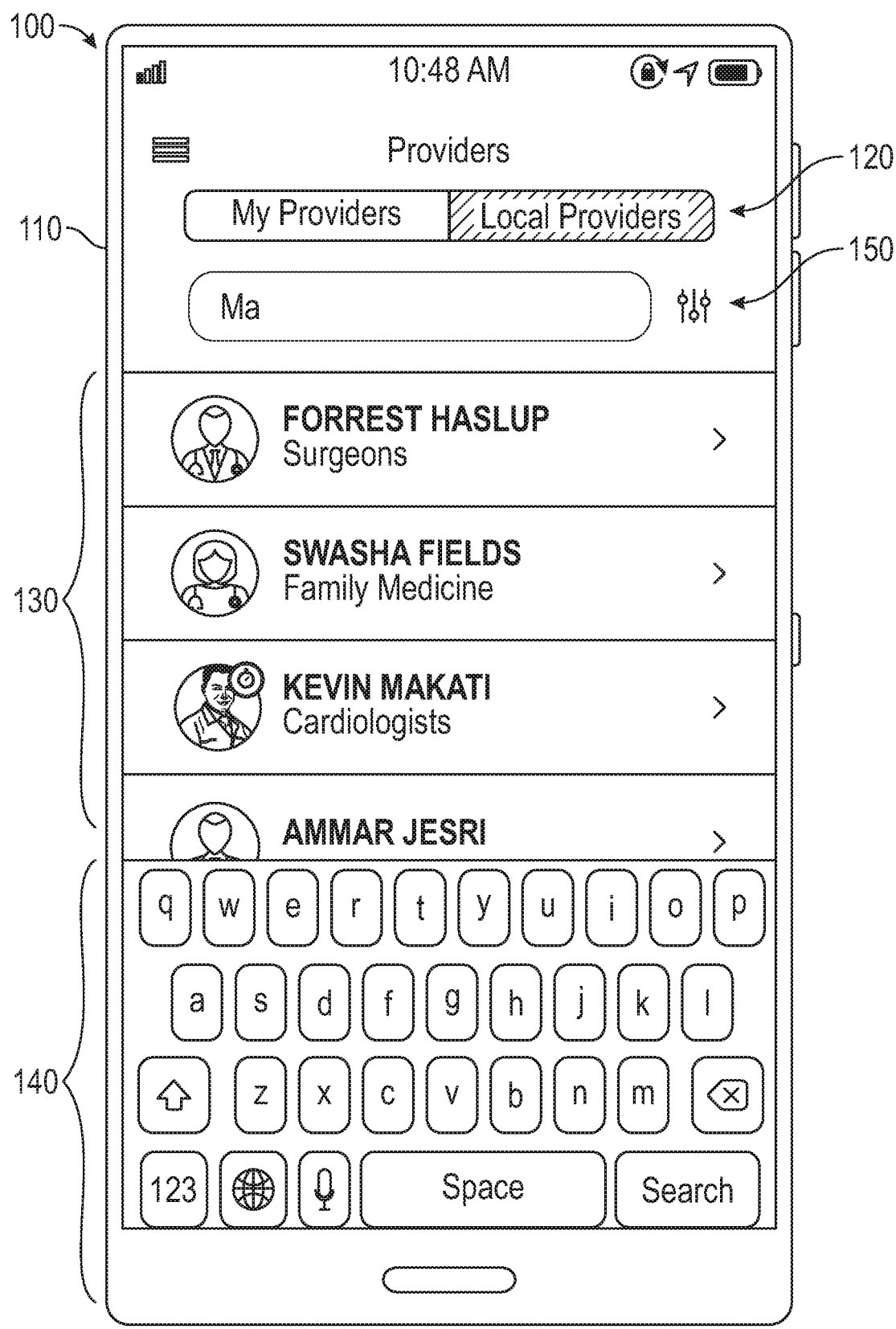
FIG. 1 is an image of a page of a DocClocker application on a mobile device, showing service provider selection by a patient, according to an embodiment of the present disclosure.

The following discussion of the embodiments of the disclosure directed to an application for measuring medical service provider wait times is merely exemplary in nature, and is in no way intended to limit the disclosed techniques or their applications or uses.

As discussed above, there is a need for an improved method of measuring wait times at a doctor's office or other medical service provider's office. There is also a need for improved real-time communication between medical staff and a patient's family/friends during a surgical procedure. The disclosed invention meets these needs by facilitating the collection of actual, verified, patient-measured wait times and aggregating them for other patients and the service provider to view, and by providing a real-time communication channel from medical staff during surgical procedures.

The invention includes a software application ("DocClocker App") running on a mobile device with Global Positioning System (GPS) capability. The DocClocker App on the mobile devices of all participating patients communicates with a back-end server which aggregates patient data, and uploads and displays the aggregate data (such as average wait time) on the DocClocker App and on the service provider's website equivalent.

The device, typically a smart phone, is carried by a patient during a visit to a medical services provider's office. The GPS identifies the patient to be within a defined "geofence" surrounding that office. A geofence is a virtual geographic boundary, defined by GPS technology, that enables software to trigger a response when a mobile device enters or leaves a particular area. The patient opens the DocClocker App and goes to that the provider's page within the App. The patient can then "Clock-In" and start the DocClocker timer. When the provider finally sees the patient, the patient can stop the DocClocker timer. It is also possible to allow the service provider to stop the timer when the patient is seen by the provider.

The elapsed time between starting and stopping the timer is considered the accuracy-enhanced wait time. The patient can post this wait time, along with a star-based review, and a comment to the provider's feed which is viewable in the App, and which also can be seen from the Internet on the provider's DocClocker webpage equivalent.

If the patient starts the DocClocker timer or stops the DocClocker timer outside of the geofence, then this time is not considered accurate and is not counted towards the provider's reported averages. This geofence feature ensures that only patients who are actually at the provider's office can measure and post wait times. This prevents the accidental usage of the DocClocker App and posting inaccurate wait times, and prevents anyone who is not actually in the designated office from intentionally posting fictitious wait time data.

If the patient starts the DocClocker timer or stops the DocClocker timer outside of the geofence, the data may still be reported to the back-end application server along with the patient's star rating and comment, however it is flagged as an inaccurate wait time post.

There is the opportunity for patients to input their appointment time to further improve the accuracy of reported wait times. Consider, for example, a patient who has a 3:00 pm appointment time but arrives at 2:30 to the office and starts the DocClocker timer. If the patient is seen at 3:05 pm and stops the DocClocker timer then, considering the 3:00 pm appointment, the reported wait time in this case would be only five minutes. If the patient has not entered their appointment time in the App, then the App would post a 35 minute wait time. Member providers would have an opportunity to flag inaccurate wait time posts; in the case being described here, the provider could enter the 3:00 pm appointment time for the patient, which would cause the measured wait time to re-compute to five minutes.

The individual patient accuracy-enhanced or geofenced wait time is averaged together with all other accuracy-enhanced wait times and is posted on the provider's DocClocker App page as "Average Clocked Wait". The individual patient/user accuracy enhanced or geofenced wait time is also posted individually alongside that patient's star rating (four out of five stars, for example) and comment on the provider's feed.

Following is a discussion of the operation of the DocClocker App which is structured around images of the application as it would appear on a smart phone screen.

FIG. 1 is an image of a page 100 of the DocClocker application showing service provider selection by a patient, according to an embodiment of the present disclosure. The page 100 appears on a screen of a mobile device 110, such as a smart phone. The device 110 includes a processor and memory configured to run application programs ("apps"), such as the DocClocker app. The device 110 further includes a GPS receiver in communication with the processor, enabling the device 110 to know its geographic location and communicate that location to any app running on the processor. The device 110 also includes other features and functional capabilities as would be understood by anyone skilled in the art—such as touch screen user interface, a timer utility, etc.

On the page 100, buttons 120 are provided to allow the user to view either a list of "my providers" or a list of local providers as identified by location. The user's "my providers" list would include service providers (doctors, dentists, physical therapists, etc.) who the user has previously added to the list, for convenient retrieval later. The local providers list would show service providers within a certain geographic radius, such as five miles.

The page 100 also includes a list section 130 in which the providers are listed based on the selection of one of the buttons 120. Providers who are subscribers to, or users of, the DocClocker app will have additional information such as a picture and the DocClocker icon displayed in the provider list section 130. The page 100—and many other pages of the DocClocker app—also includes a keyboard 140 for allowing a user to enter information, such as in a Search field 150.

Figure 2:
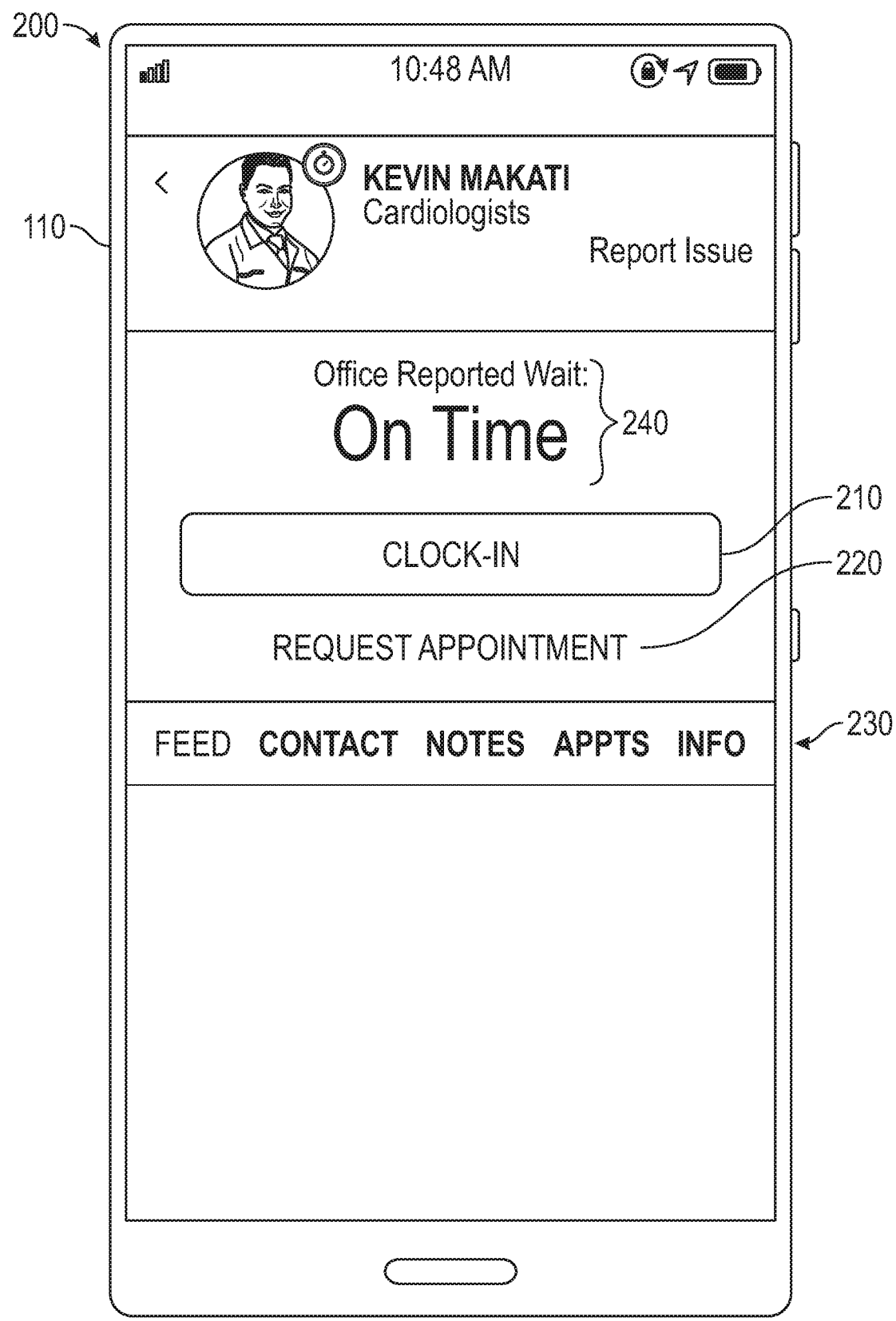
FIG. 2 is an image of a page of the DocClocker application showing a selected service provider's current status and allowing the patient to schedule an appointment or begin wait time monitoring.

FIG. 2 is an image of a page 200 of the DocClocker application showing a selected service provider's current status and allowing the patient to schedule an appointment or begin wait time monitoring, according to an embodiment of the present disclosure. The page 200 is what would be displayed when the user selects a provider from the list section 130 of FIG. 1. The page 200 includes a Clock-In button 210 to allow the user to begin wait time measurement, discussed below. The Clock-In button 210 would be used if the user is at the provider's office (either with an appointment or as a walk in), and ready to begin a wait time clock. The page 200 also includes a Request Appointment button 220, which would be used if a user wishes to make an appointment with the provider selected from the list section 130.

The page 200 (and other pages discussed later) also includes a tab bar 230, which is a bar or ribbon containing different page tabs of the DocClocker application which may be selected. The page 200 is the provider's Feed page, discussed further below. Also shown on the Feed page 200 is a Wait Time display 240. The Wait Time display 240 is a dynamic section which displays information from a back-end DocClocker server. The displayed wait time may be office-reported (as shown in FIG. 2), or it may be an average of actual patient-measured times (discussed later). The Wait Time display 240 may show "On Time" if the wait time is below a certain threshold, such as ten minutes. The Wait Time display 240 may display ranges, such as 15-20 minutes, or actual values in integer minutes for example. Office-reported wait times may be configured to always display ranges, while patient-measured wait times may be configured to always display an integer number (average of reported values).

Figure 3:
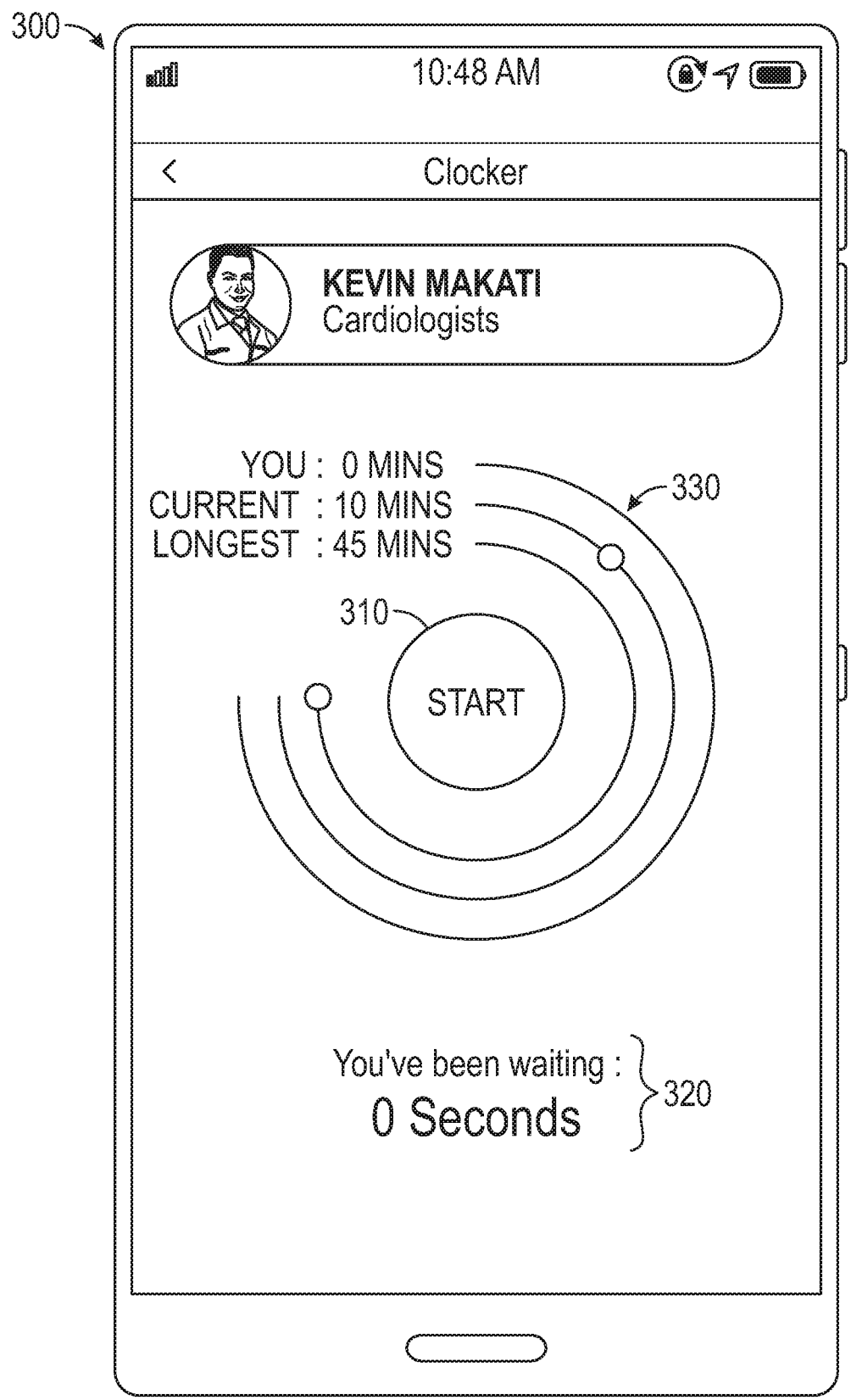
FIG. 3 is an image of a page of the DocClocker application showing the selected service provider's wait time statistics and allowing the patient to start a wait time clock.

FIG. 3 is an image of a page 300 of the DocClocker application showing the selected service provider's wait time statistics and allowing the patient to start a wait time clock or timer, according to an embodiment of the present disclosure. The page 300 includes a Start button 310, which is tapped by the user to begin clocking wait time. In a preferred embodiment, the Start button 310 would not be active unless the user is within the geofence of the service provider's office location. The page 300 also includes a Wait Time Display 320, where the actual wait time in minutes and seconds is displayed after the user presses the Start button 310.

The page 300 further includes a Wait Time Comparator 330, which in one embodiment includes three concentric circular arcs representing the user's actual wait time, the current average measured or office-reported wait time, and the longest measured wait time within a preceding time window (such as the preceding four hours). Each of the arcs in the Comparator 330 is sized to a common arc-angle scale—such as where 45 minutes is represented by a ¾ circle arc as shown in FIG. 3. Each of the arcs in the Comparator 330 also has near it's 12:00 position a textual display of the respective time value. Other types of displays may be used as suitable for the Wait Time Comparator 330—such as vertical bars, etc.

Figure 4:
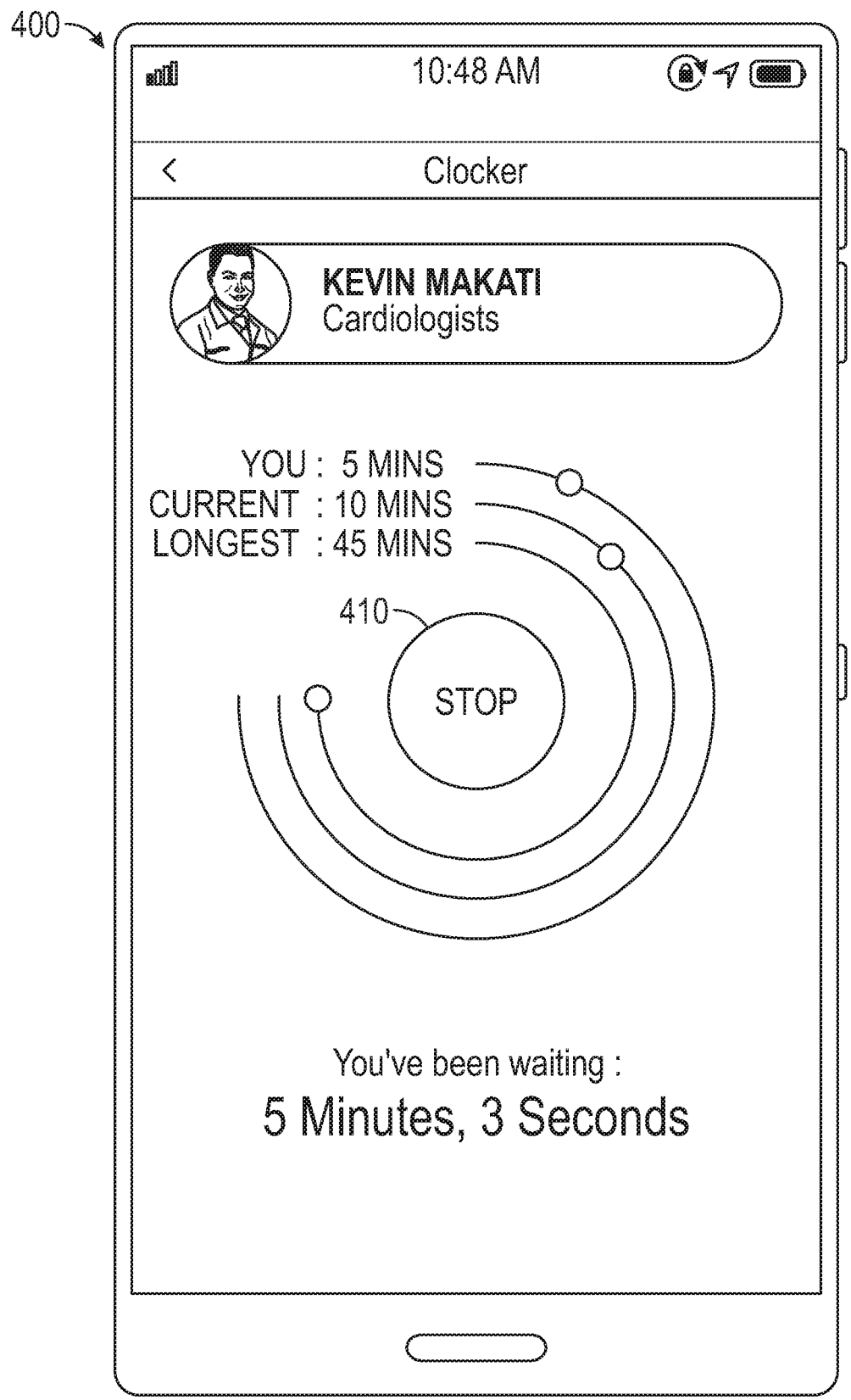
FIG. 4 is an image of a page of the DocClocker application showing the selected service provider's wait time statistics and allowing the patient to stop the wait time clock.

FIG. 4 is an image of a page 400 of the DocClocker application showing the patient's running wait time, the selected service provider's wait time statistics and allowing the patient to stop the timer, according to an embodiment of the present disclosure. Now that the wait time clock is running, the page 400 has replaced the Start button 310 of FIG. 3 with a Stop button 410. Other parts of the Wait Time Comparator 330 remain the same as in FIG. 3, however the current average and longest times may be updated in real time based on new data from the back-end server.

Figure 5:
FIG. 5 is an image of a page of the DocClocker application after the clock has been stopped, allowing the patient to post the wait time, a rating and a comment.

FIG. 5 is an image of a page 500 of the DocClocker application after the timer has been stopped, allowing the patient to post the wait time, a star-based rating and a comment, according to an embodiment of the present disclosure. The page 500 appears after the Stop button 410 is pressed on the page 400. An actual measured wait time 510 is displayed near the top; this is the value of the elapsed time between the user pressing the Start button 310 and pressing the Stop button 410. The measured wait time 510 also includes a comparative note indicating whether the user's actual wait time is longer, shorter or about the same as the current average for the selected service provider.

The page 500 also includes a comments section 520, allowing the user to enter comments as he/she may desire. The page 500 further includes a star-based rating section 530, where the user may indicate a rating such as four out of five stars. In addition, the page 500 includes posting option buttons 540, where the user may post all of the above information (wait time, comments and rating) anonymously or attributed to the user's account profile. A cancel button 550 is also available, which may be used if the user does not wish to post the wait time and other information to the DocClocker back-end server at all.

Figure 6:
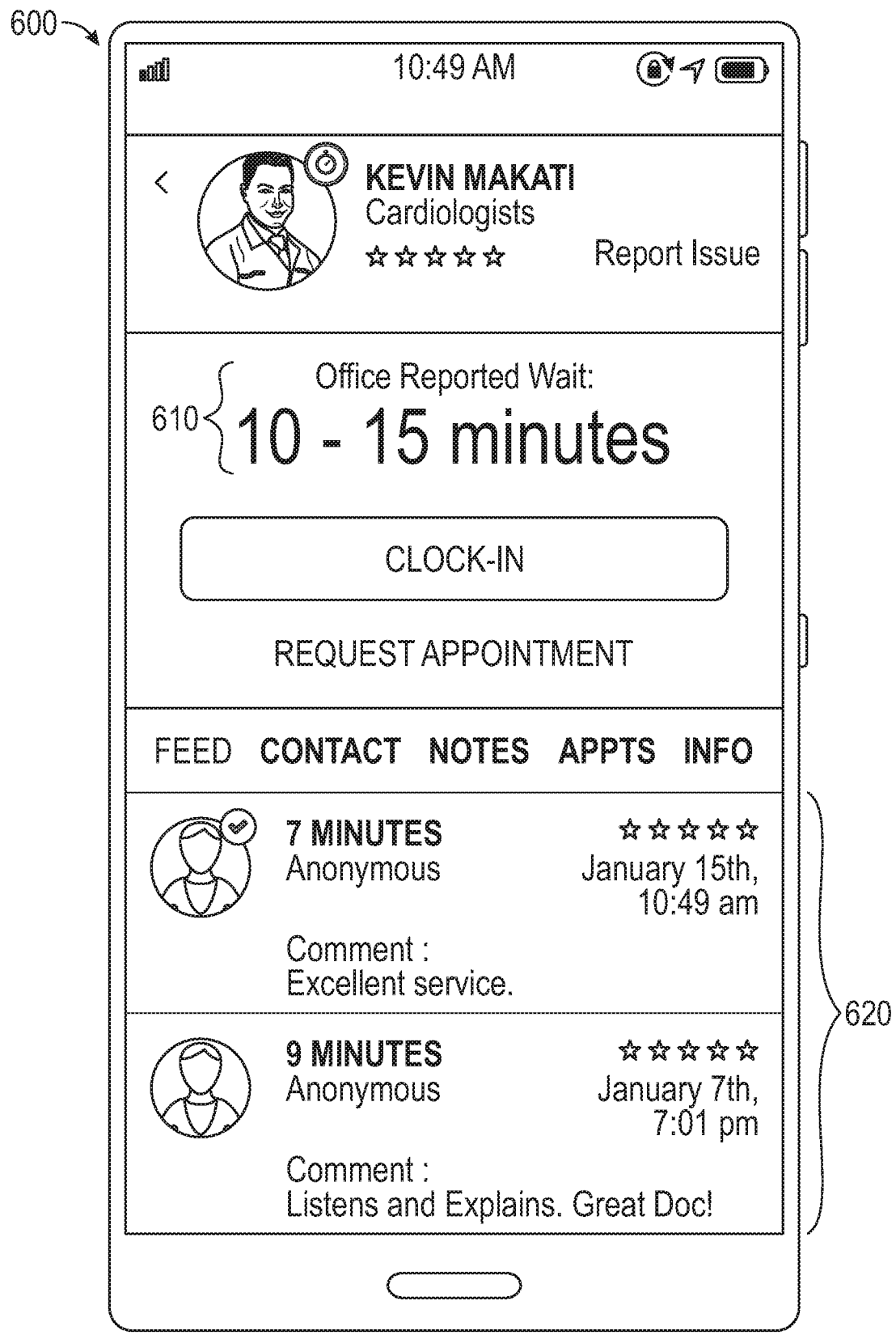
FIG. 6 is an image of a page of the DocClocker application showing the selected service provider's feed containing patient-posted wait time data, ratings and comments.

FIG. 6 is an image of a page 600 of the DocClocker application showing the selected service provider's Feed page containing patient-posted wait time data, ratings and comments, according to an embodiment of the present disclosure. The Feed page 600 is an updated version of the Feed page 200 discussed earlier. The Feed page 600 reflects data available after several or many users have posted their information as shown in FIG. 5. The Feed page 600 includes an office-reported average wait time at 610. In section 620, the Feed page 600 shows user postings for the subject service provider. The displayed user postings include actual measured wait time, comments and star-based rating, as discussed earlier. The displayed user postings may be sorted and filtered in any suitable manner, such as sorted to show most recent at the top, and filtered to show only a preceding time window such as six months.

Figure 7:
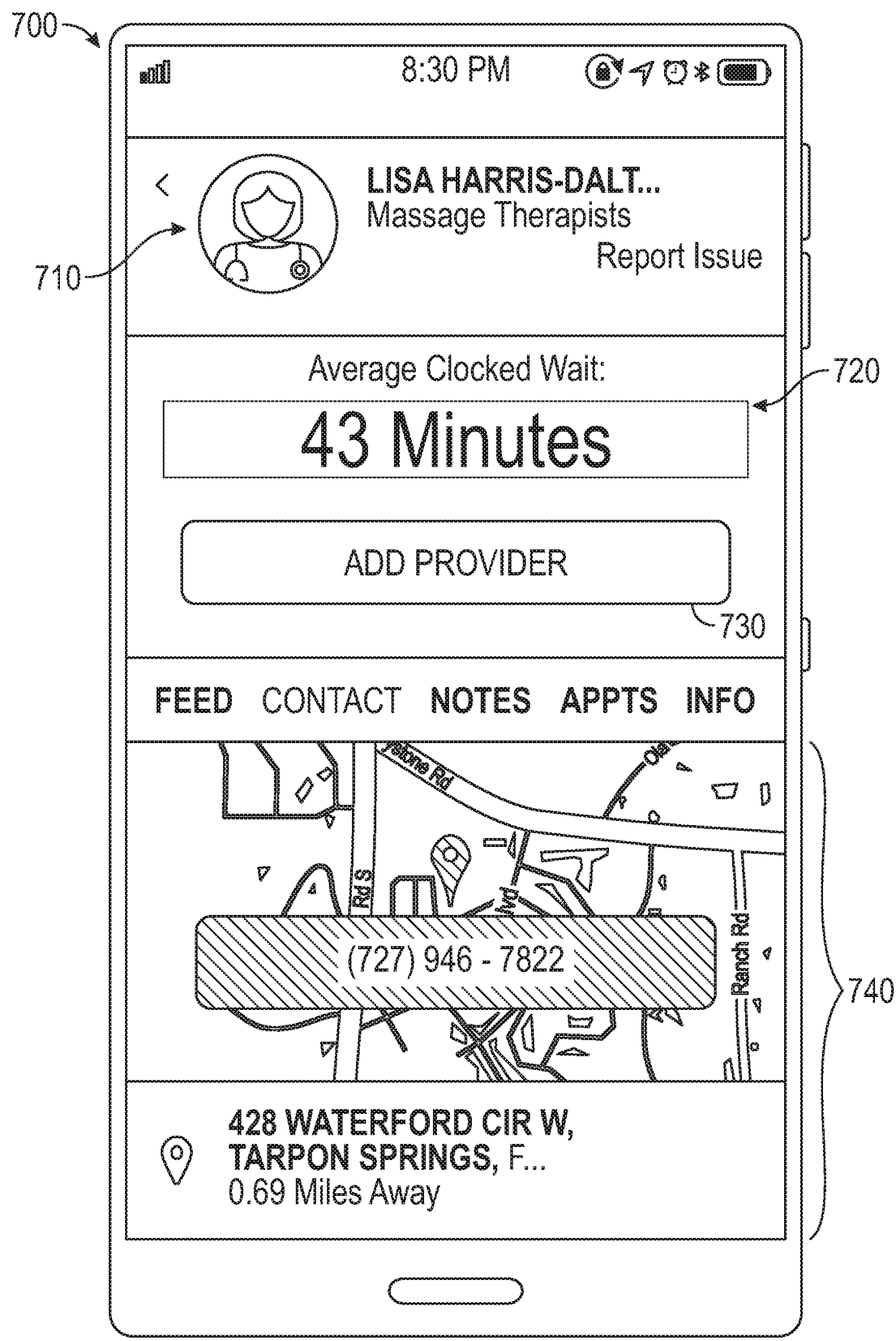
FIG. 7 is an image of a page of the DocClocker application showing a service provider's contact page including map, address and phone number information.

FIG. 7 is an image of a page 700 of the DocClocker application showing a service provider's contact information—including map, address and phone number information, according to an embodiment of the present disclosure. The contact page 700 is selected by tapping "Contact" in the tab bar 230 discussed earlier. The contact page 700 includes the provider's name and title in a section 710 at the top, along with a photograph if available. The photograph may only be available if the provider is a subscriber to the DocClocker app. The contact page 700 also includes a Wait Time section 720, which in this case displays average clocked wait time as an integer number of minutes, not a range. The service provider, if a DocClocker subscriber, can use their administrative tools to define whether the average actual time is displayed in the section 720, or an office-reported range.

The contact page 700 also includes a button 730 which the user can press to add the currently-displayed service provider to the user's "My Providers" list shown previously. At the bottom of the contact page 700, typical contact information is displayed in a section 740—including a map with option to click on and start navigation in a map app, phone number which may be clicked to call the provider's office, street address and distance information.

Figure 8:
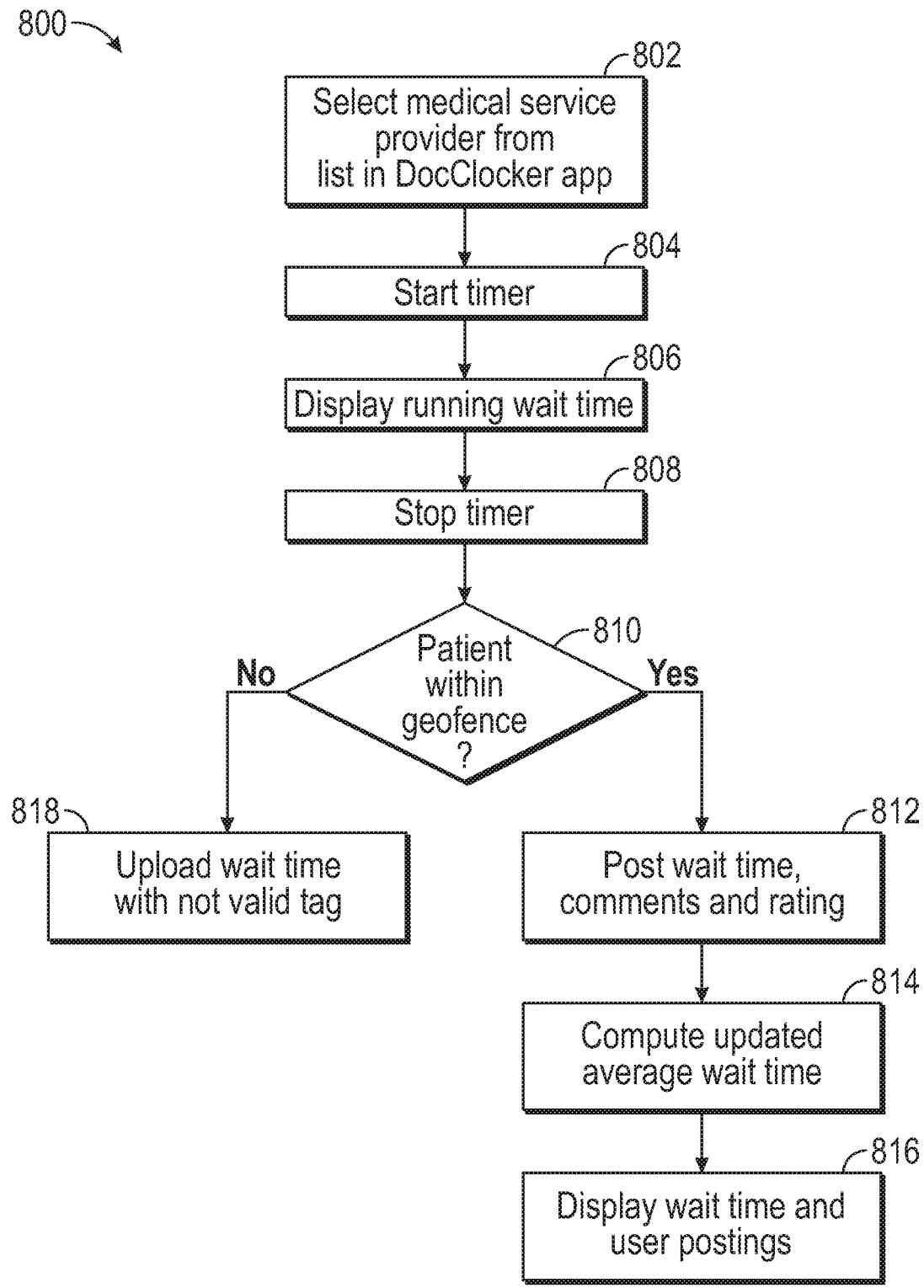
FIG. 8 is a flowchart diagram of a method for patient measurement and reporting of medical service provider wait time, according to embodiments of the present disclosure and FIGS. 1-7.

FIG. 8 is a flowchart diagram 800 of a method for patient measurement and reporting of medical service provider wait time, according to embodiments of the present disclosure and the screen images of FIGS. 1-7. After launching the application, at box 802, the patient selects a medical service provider from a list. As shown in FIG. 1, the list may be a list of "my providers" previously identified by the patient, or the list may be a list of local providers whose office is within a selected distance of the patient's current location. As shown in FIG. 2, once the provider is selected, the application displays the provider's Feed page, where the patient can either schedule an appointment or begin using the clocking feature. Providers may subscribe to the DocClocker App service, which gives the subscribing provider access to their data on the application server, including the ability to define an "Office Reported Wait" time value as seen in FIG. 2 below the provider's name and picture. The Office Reported Wait may be set to "On Time", or may be defined as a range such as 15-30 Minutes. Office-reported wait time ranges and actual measured average wait times may also advantageously be color coded for display in DocClocker—with times less than 30 minutes being green, times from 30-60 minutes being yellow, and times over 60 minutes being orange, for example.

At box 804, the patient starts a timer to begin measuring wait time. This step is shown in FIG. 3, which is what is displayed after the patient selects "Clock In" on the image of FIG. 2. At the box 804, the patient presses the Start button to begin the timer. At box 806, the application displays a running wait time for the patient, a current average wait time for the provider and a current maximum wait time for the provider. As shown in FIG. 3, the three times may be displayed as concentric circular arcs around the Start button. The small circle on the outer arc (running wait time) moves around the arc in real time. The current average and current maximum arcs may be truncated at the designated time, or may include a small circle or other marker at the designated time. In one embodiment as shown in FIG. 3, the three concentric arcs have different lengths but each subtend an angle of 270° (¾ of a circle). In such an embodiment, the time-scale of the arcs may be configured such that the terminal end of each arc represents the same amount of time, such as 45 minutes. Other time-scaling configurations of the arcs, and other graphic timing indicators, are also possible.

The current average wait time is the rolling average of patient-posted wait times for the selected service provider over a certain time window—such as the past two hours or four hours. The current maximum wait time is the longest patient-posted wait time for the selected service provider recorded during the same time window or a different recent time window.

At box 808, the patient presses the Stop button to stop the timer to produce a final wait time. This step, shown in FIG. 4, is performed when the patient is admitted to see the provider. At decision diamond 810, the application verifies or determines whether the patient was located within the predetermined geofence area defined around the office location of the selected provider when the timer was started and stopped.

At box 812, the application reports the final wait time for this patient visit to the application server, if the patient was located within the geofence area when the timer was started and stopped. This step is performed when the patient presses either the "Post Anonymously" or the "Post Using Profile" button as shown in FIG. 5. Posting anonymously does not send patient identification information to the server for display. At this point, the patient can also choose to provide comments about the service provider and rate the experience using a 5-star rating scale.

At box 814, the application server calculates an updated value of the average wait time for the provider using the final wait time and previously reported patient wait times within the rolling average time window. The final wait time for the current patient is only included in provider average wait time calculations if the patient was located within the geofence area when the timer was started and stopped.

At box 816, the application server displays the average wait time and other information about the provider on the provider's Feed page in the application, where it can be viewed by a plurality of other patient mobile devices communicating with the application server. This is shown in FIG. 6. The calculated average wait time is displayed on the Feed page for non-subscribing providers, while subscribing providers may view the calculated average wait time on the application server and use that value in defining their office-reported wait time. The provider's Feed page in the application shows the current average wait time below the provider's name (FIG. 6 shows an office-reported wait, which is currently "On Time"), and shows individual posted wait times, comments and ratings at the bottom. This page also allows a patient to request an appointment. At box 818, the application may upload wait time data to the server even if the patient is outside the geofence when the timer is started or stopped. However, in this case, the patient's final wait time figure will be flagged as not being valid and will not be included in average wait time calculations.

FIG. 7, discussed earlier, shows a Contact page for a non-subscribing provider in the DocClocker App. The Contact page, like the Feed page, includes the average patient-measured wait time at the top (either the calculated average for a non-subscriber or an office-reported average for a subscriber), along with typical contact information such as address and phone number of the provider's office, and a map. Other pages, which may be associated with a particular provider, are also included in the DocClocker App. This is also shown in FIG. 7, where the other pages include a Notes page, an Appointments page and a general information page.

In any application where the general public has the ability to input data, there is an opportunity for inaccurate information to be entered. The geofence feature described above goes a long way toward ensuring that only patients who are present in the provider's office upload wait times. However, it is still possible that a patient might forget to stop the timer, for example, until ½ hour after being taken back to an exam room. This error would reflect badly on the provider, so the DocClocker App provides features to allow the provider to prevent or correct such errors. One feature is the ability for a subscribing provider (typically an office manager or assistant) to stop the clock at the moment the patient is called back to the exam room. This could be done from a computer communicating with the application server. Another feature would allow subscribing providers to view data entries and delete any which are obviously inaccurate. These features make it more likely for providers to want to participate in the usage of the DocClocker application, which then provides the benefit of real-time, patient-monitored wait time feedback to the patients.

All of the features for configuration and management of DocClocker data, for subscribing service providers, are available through an administrative application or web page. The office manager or assistant would authenticate into the service provider's DocClocker account and define configuration settings (several of which have been discussed above), identify inaccurate user postings, etc.

As discussed above, actions must be taken by the patient in order to measure and upload wait times, and actions are taken by the application server based on the uploaded measurements. Additional actions may be triggered by the uploading of patient wait times, comments and ratings. For example, the application server may flag any wait time or rating that requires the attention of the subscribing service provider, and send a notification to the service provider requiring a review of the flagged items and a disposition (mark the items as valid or invalid). Flagged items for review may include, for example, wait times which are dramatically different than average, wait times which exceed the current maximum, ratings below 3 stars, etc.

The DocClocker application, like many mobile apps, is an ideal platform for attracting advertising revenue. The incorporation of advertisements can work to the advantage of both the application hosting service and the subscribing service providers. For example, subscribing service providers can be advertised when a user is looking for a provider for a service for which they do have a preferred provider. All other types of context-specific and general advertising content is also readily incorporated in DocClocker, as would be understood by anyone skilled in development of mobile or web apps.

The Request Appointment button 220 of FIG. 2 may be configured to operate in more than one way. For non-subscribing providers, the Request Appointment button 220 may simply provide a pop-up allowing the user to call the provider's office at the known phone number. For subscribing providers, some may wish to integrate their master appointment booking database with the DocClocker back-end server, thus making known available appointments known in semi-real-time to the DocClocker server, and enabling a user to immediately see available appointment openings when clicking the Request Appointment button 220. Other subscribing providers may not want to integrate their master appointment booking database with DocClocker, but may choose to allow a user to book an appointment in one step by allowing DocClocker to book appointments in time windows which historically have short wait times based on actual measured data. For example, if a provider almost always has wait times less than 15 minutes between 9:00 and 11:00 am on weekdays, that provider may choose to allow DocClocker to schedule 1-2 appointments per day during that window, without requiring a 2-step request/confirm procedure. Still other service providers may wish to use the Request Appointment button 220 to allow the user to request an appointment at one or more desired times, but then require a confirmation or change notification from the service provider's office (performed through the administrative page).

Other features may also be integrated with the DocClocker App. One advantageous feature is the ability for a physician who is a subscriber to the DocClocker App to use a tablet-only application (DOC-OR) to broadcast one-way, encrypted Operating Room (OR) updates to a patient's friends and family using the DocClocker App. The communication is handled through the DocClocker back-end server and its normal communication channels to DocClocker app users.

The DOC-OR portion of the DocClocker application works as follows. A tablet device such as an iPad is configured with the DOC-OR application and fitted in a sterilizable case. The tablet goes with the patient to the pre-op area where family members are permitted, where the family provides consent for sending status messages through DOC-OR. The family members then provide phone numbers at which they wish to receive updates. The phone numbers are entered in DOC-OR/DocClocker, which sends confirmation codes to those phones, which must have the DocClocker App loaded. The family members enter their unique code into DocClocker to make the handshake and initiate the messaging session from DOC-OR to the family members' phones.

The DOC-OR tablet itself stays with the patient—moving from pre-op to the OR to post-op and recovery. One or more medical staff are assigned to send status messages at various times in the procedure. In the OR itself, the tablet would be located at a side location away from the surgical table, where a medical assistant or anesthesiologist or other person can send the DOC-OR messages.

Figure 9:
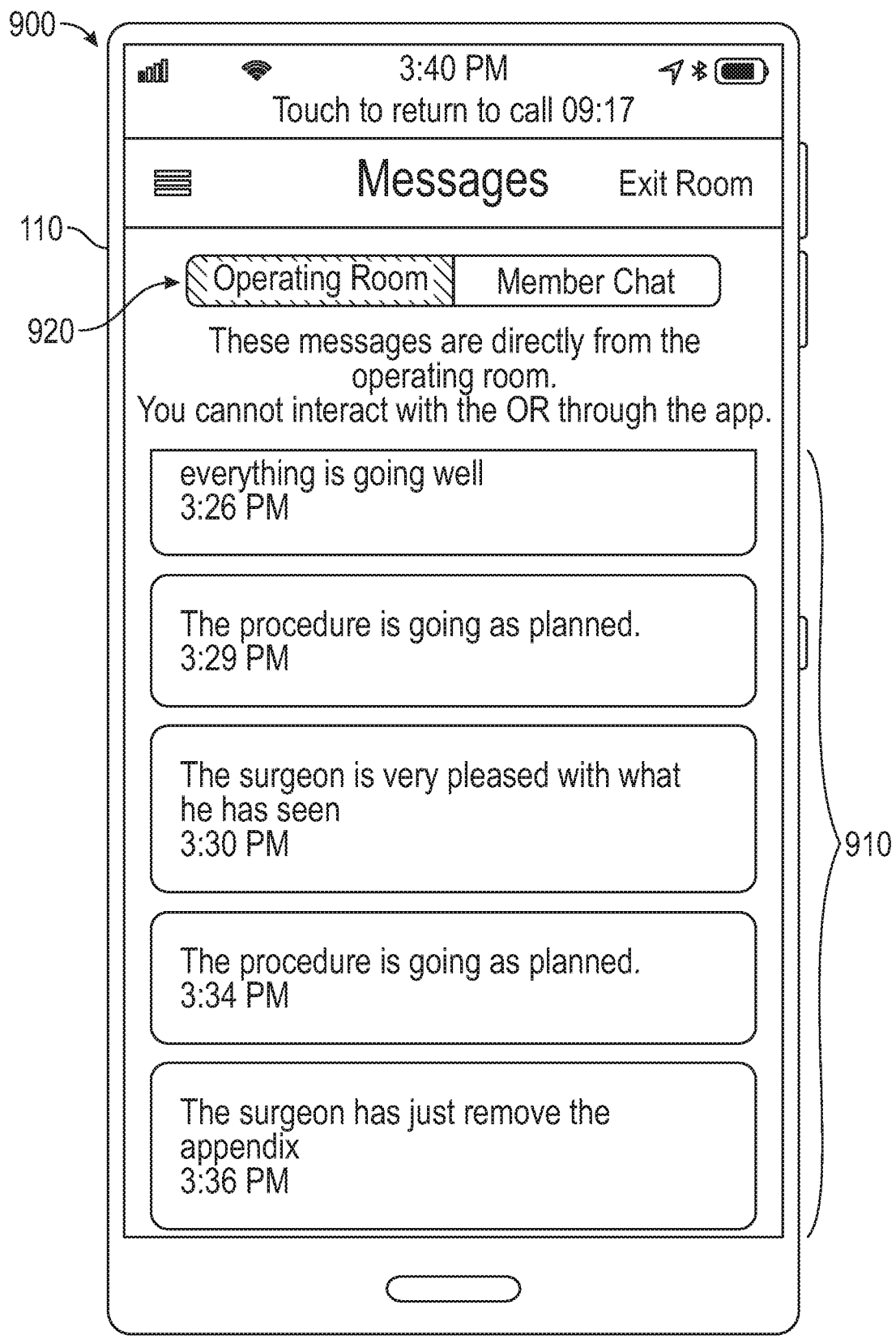
FIG. 9 is an image of a page of the DOC-OR portion of the DocClocker application on a mobile device, showing a series of messages that a patient's family might receive during an operation, including pre-op, OR, post-op and recovery.

FIG. 9 is an image of a page 900 of the DOC-OR portion of the DocClocker application showing a series of messages that the patient's family might receive during an operation, including pre-op, OR, post-op and recovery, according to an embodiment of the present disclosure. The page 900 is viewed by friends/family using the DocClocker app on the mobile device 110. Messages are displayed in chronological order in a section 910. Many DOC-OR messages are pre-defined for the various stages of the procedure—including procedure-specific messages like "We have started the procedure and everything is going well", and "The surgeon has just removed the appendix". Medical staff who send DOC-OR messages do not have to type the text for most messages—they simply select an appropriate message from a menu. Custom messages may also be typed and sent at any time. Photographs may also be sent through the DOC-OR messaging system, preferably using the camera available on the tablet device.

The page 900 also includes buttons 920 for the user to select whether to view the OR-sent messages (as shown in FIG. 9) or view a member chat window. The member chat window is a private chat session between family and friends (all DocClocker app users) who are registered for this particular patient's procedure. The member chat window allows those family and friends to chat amongst themselves online, while checking back on the OR message page from time to time.

Figure 10:
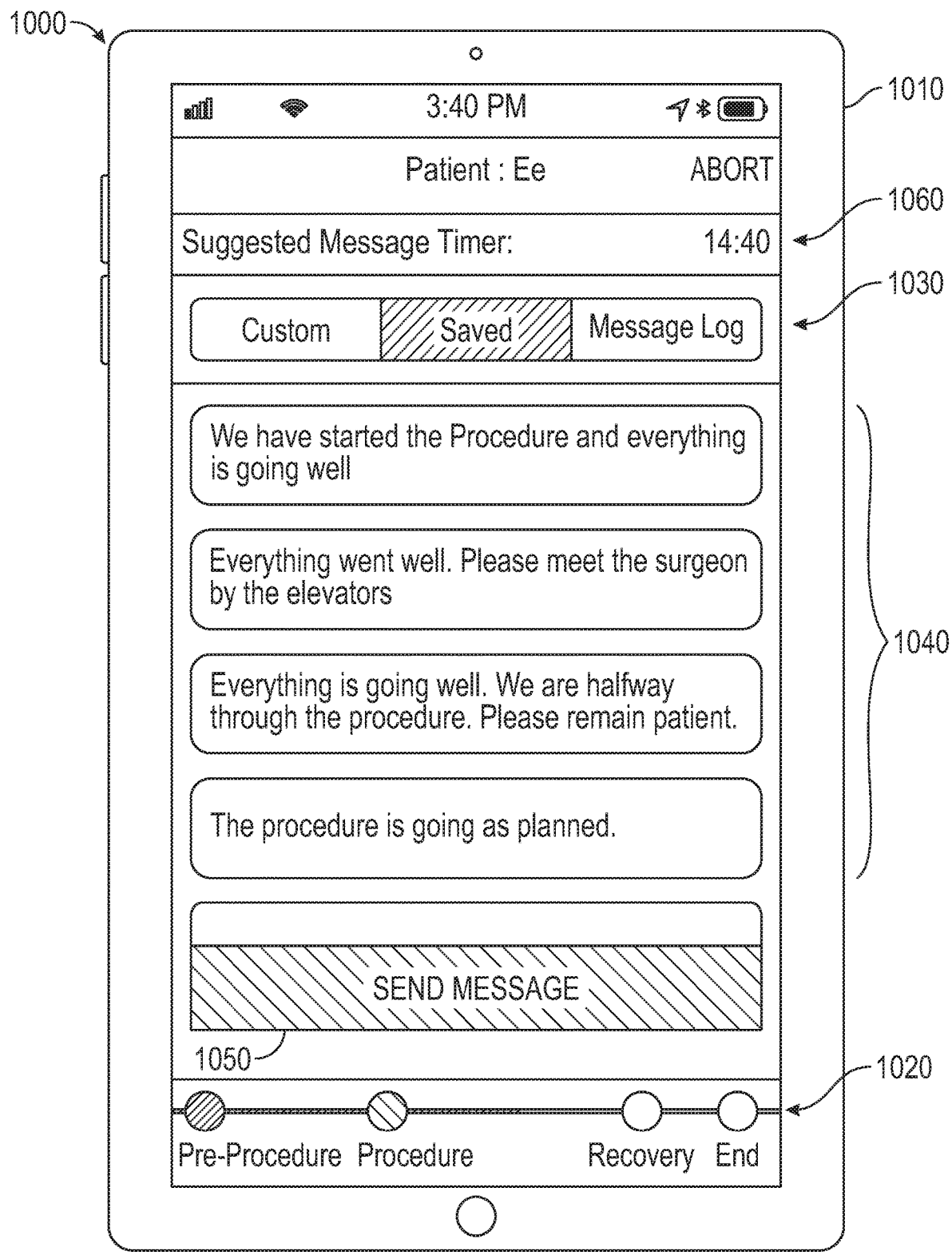
FIG. 10 is an image of a page of the DOC-OR application on a tablet device as it would be used by medical staff in the OR, showing a list of pre-defined, procedure-specific messages available to send to the patient's friends and family.

FIG. 10 is an image of a page 1000 of the DOC-OR application on a tablet device 1010 as it would be used in the OR, showing a list of pre-defined, procedure-specific messages available to send to the patient's friends and family, according to an embodiment of the present disclosure. A phase bar 1020 at the bottom of the page 1000 is used by medical staff to select what phase the procedure is in—such as pre-procedure, procedure, recovery, etc. In any phase, medical staff may click on a message and send it, or type in a custom message, from this screen of DOC-OR. Buttons 1030 are used to select either "Saved" (predefined) messages, in which case a message list 1040 is displayed, or "Custom" messages, in which case a keyboard is displayed on the tablet 1010 to allow a custom message to by typed. For either Saved or Customer messages, a Send button 1050 is provided; when the Send button 1050 is pressed, the message is sent to the DocClocker users who are registered for the procedure, as discussed above.

A suggested message count-down timer 1060 may also be provided, to remind the medical staff when it is time to send an update message to the users who are monitoring the procedure using DocClocker/DOC-OR.

An administrative web portal to the DOC-OR application server offers features to a subscribing physician such as defining providers (doctors) in the system, buying the DOC-OR tablet devices and subscribing to a monthly service for the application, configuring messages available for each medical procedure and room, managing consent forms, and analyzing data and statistics related to DOC-OR usage.

Figure 11:
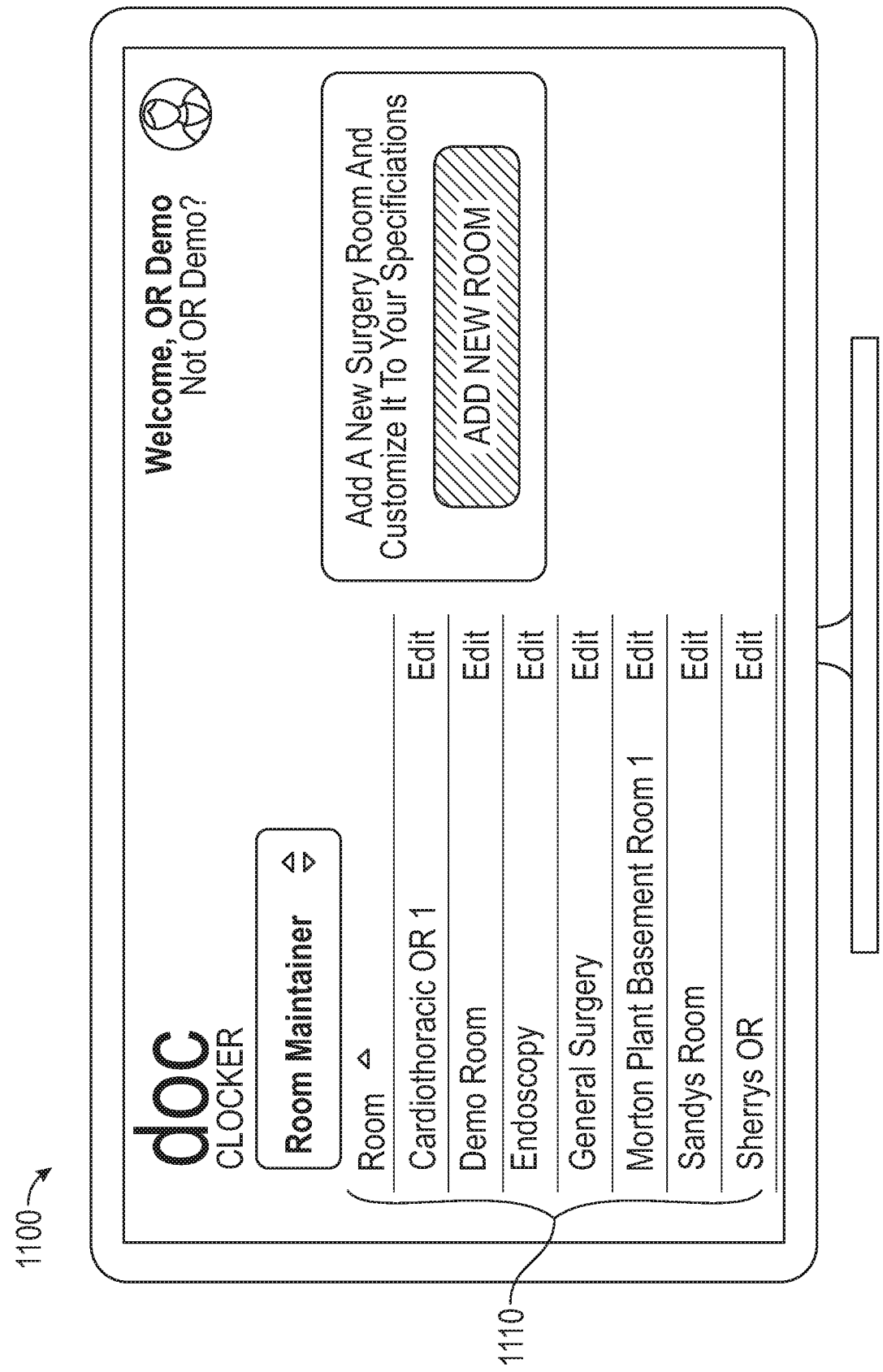
FIG. 11 is an image of an administrative web portal to the DOC-OR application server, showing how procedure rooms are defined for a provider or a team of providers.

FIG. 11 is an image of a page 1100 of the DOC-OR administrative web portal showing how procedure rooms are defined for a provider or a team of providers, according to an embodiment of the present disclosure. The page 1100 may be displayed on a web browser on a computer or on the tablet device 1010. In the example shown in FIG. 11, various operating rooms are defined in a section 1110, each having either a general surgical function or a specific type of procedure such as endoscopy.

Figure 12:
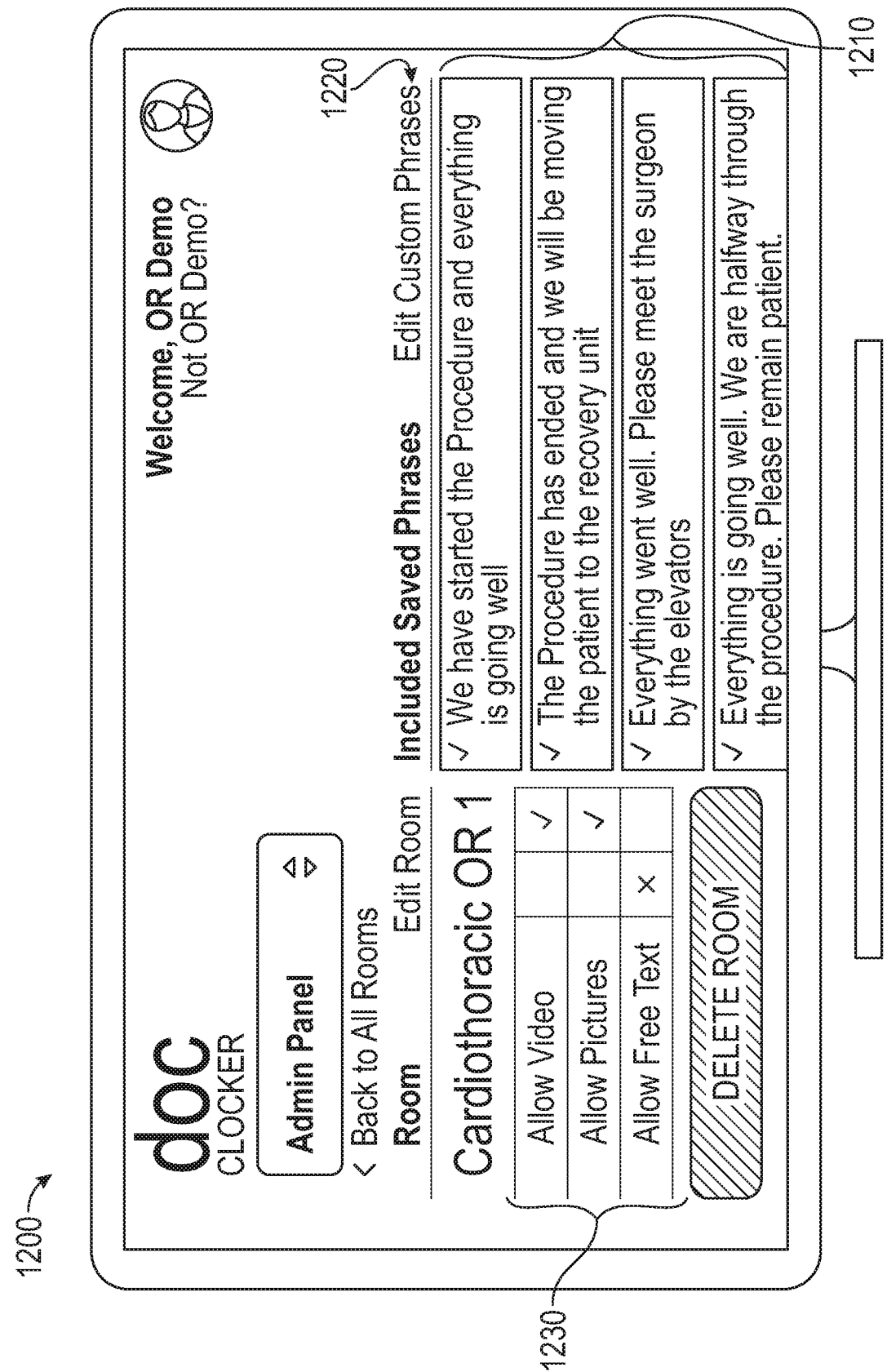
FIG. 12 is an image of the DOC-OR administrative web portal showing how pre-defined messages are created for one of the procedure rooms shown in FIG. 11.

FIG. 12 is an image 1200 of the DOC-OR administrative web portal showing how pre-defined messages are created for one of the procedure rooms shown in FIG. 11, according to an embodiment of the present disclosure. In the example shown in FIG. 12, the specific operating room is a cardiothoracic OR, and the pre-defined messages shown at 1210 include content such as "Everything is going well" and "The procedure has ended and we will be moving the patient to the recovery unit". Buttons 1220 allow the administrative user to show Saved (pre-defined) messages (as shown) or define new messages. Each operating room has a set of option selectors 1230, where options such as sending pictures, sending video and sending custom text messages are definable as yes or no by way of a check box.

Each of the different operating rooms and procedure types of FIG. 11 can have a unique list of the pre-defined saved messages shown in FIG. 12. Furthermore, the pre-defined saved messages are attributed to the procedure phases shown in the phase bar 1020 of FIG. 10. In other words, the message "The Appendix has been successfully removed" would only be available in the Procedure phase, not in the Pre-Op phase.

By using the DOC-OR features of the DocClocker system discussed above, doctors who specialize in surgical procedures can offer even more convenience and service to their patients in the form of real-time updates during surgery.

Figure 13:
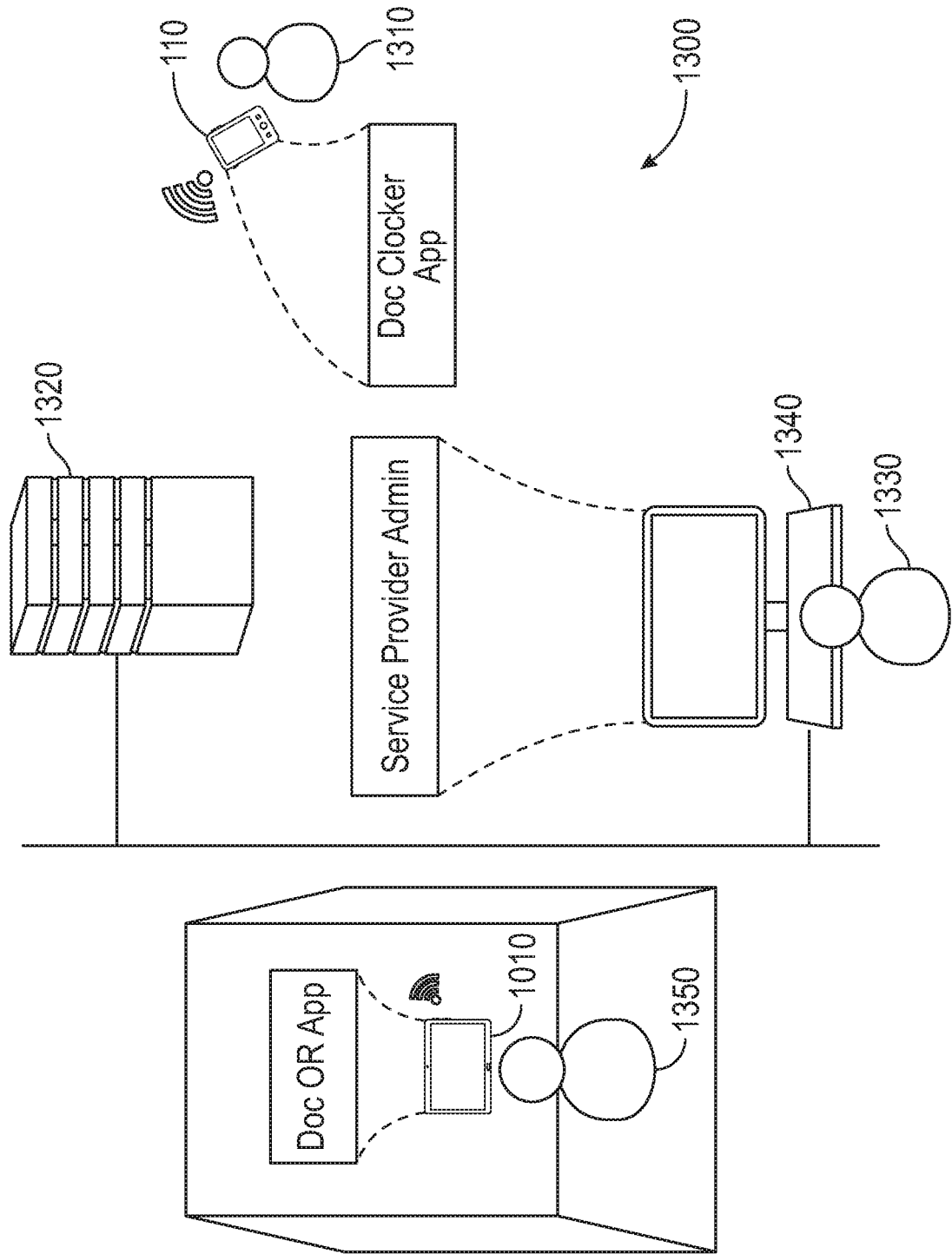
FIG. 13 is a diagram of an architecture for the DocClocker system, according to embodiments of the present disclosure.

FIG. 13 is a diagram of an architecture 1300 for the DocClocker system, according to embodiments of the present disclosure. A user 1310 with the mobile device 110 accesses the DocClocker app as discussed above. The mobile device 110 is in wireless communication with a back-end server 1320 which stores the data for DocClocker and runs all of the back-end computations, as discussed above. A user 1330 at a service provider uses a computer 1340 to perform administrative functions for that service provider's DocClocker presence. For example, as discussed above, the service provider admin may select whether to display office-reported wait times or user-measured wait times, and may determine whether some user measurements are inaccurate. The computer 1340 is in communication with the back-end server 1320, typically via the Internet and various local area networks.

A user 1350 with the tablet device 1010 accesses the DOC-OR application. The tablet device 1010 is also in wireless communication with the back-end server 1320. The wireless communication of the tablet device 1010 and the mobile device 110 may be by Wi-Fi, cellular, or any other suitable wireless communication type. The user 1350 may be using the DOC-OR app to communication real-time status information during a surgery, or to set up predefined messages, as discussed previously. Messages sent by the user 1350 during a procedure are received by the user 1310 of the DocClocker app on the mobile device 110.

It is to be understood that the software applications and modules described above are executed on one or more computing devices having a processor and a memory module. For example, the DocClocker application itself runs on the processor in a mobile device such as a smart phone, in a manner well known in the art. The DOC-OR portion of the DocClocker application similarly uses a tablet device with processor and communication capabilities, as known in the art. Likewise, the application server is a server computer with processors and memory and is configured to communicate with all users of the DocClocker app, receive data from and send data to those users. Furthermore, the communication between the mobile devices and the application server may use any suitable technology—such as a cellular phone/data network, Wi-Fi, the Internet, etc.

The foregoing discussion describes merely exemplary embodiments of the disclosed methods and systems. One skilled in the art will readily recognize from such discussion and from the accompanying drawings and claims that various changes, modifications and variations can be made therein without departing from the spirit and scope of the disclosed techniques as defined in the following claims.

What is claimed is:

1. A method for measuring and reporting medical service provider wait times, said method comprising:
   selecting a medical service provider, by a patient using a mobile device running an application, where the mobile device has Global Positioning System (GPS) capability and the mobile device communicates with an application server;
   starting a timer to begin measuring wait time, by the patient using the application;
   displaying, by the application running on the mobile device, a running wait time for the patient, a current average wait time for the provider and a current maximum wait time for the provider;
   stopping the timer to produce a final wait time, by the patient using the application, when the patient is admitted to see the provider;
   verifying, by the application, that the patient was located within a predetermined geofence area defined around an office location of the selected provider when the timer was started and stopped;
   reporting the final wait time to the application server, by the application, if the patient was located within the geofence area when the timer was started and stopped;
   calculating, by the application server, an updated value of the average wait time for the provider using the final wait time and previously reported patient wait times; and
   displaying, using the application running on a plurality of patient mobile devices communicating with the application server, the average wait time and other information about the provider on a provider's feed page in the application.

2. The method according to claim 1 further comprising inputting, by the patient using the application, a rating of the provider and a comment about the provider.

3. The method according to claim 2 further comprising uploading the rating and the comment to the application server from the mobile device, and displaying the final wait time, the rating and the comment on the provider's feed page in the application.

4. The method according to claim 1 further comprising stopping the timer to produce the final wait time, by the provider using a computing device communicating with the application server.

5. The method according to claim 1 further comprising entering an appointment time, by the patient using the application.

6. The method according to claim 5 further comprising downwardly revising the final wait time, by the application, if the timer was started before the appointment time.

7. The method according to claim 1 wherein displaying a running wait time for the patient includes displaying the running wait time, a current average wait time and a current maximum wait time as three concentric circular arcs centered around a start/stop button on a display of the mobile device.

8. The method according to claim 1 wherein displaying the average wait time on a provider's feed page includes displaying the updated value of the average wait time calculated by the application server for non-subscribing providers, and displaying an office-reported wait time for subscribing providers.

9. A system for measuring and reporting medical service provider wait times, said system comprising:
   an application server having a processor and memory; and
   a plurality of mobile devices each having a processor and memory and Global Positioning System (GPS) capability, said mobile devices being in communication with the application server,
   where the processors on the application server and the mobile devices are configured with algorithms to perform steps including;
   selecting a medical service provider, by a patient using one of the mobile devices running an application;
   starting a timer to begin measuring wait time, by the patient using the application;
   displaying, by the application running on the one mobile device, a running wait time for the patient, a current average wait time for the provider and a current maximum wait time for the provider;

stopping the timer to produce a final wait time, by the patient using the application, when the patient is admitted to see the provider;

verifying, by the application, that the patient was located within a predetermined geofence area defined around an office location of the selected provider when the timer was started and stopped;

reporting the final wait time to the application server, by the application, if the patient was located within the geofence area when the timer was started and stopped;

calculating, by the application server, an updated value of the average wait time for the provider using the final wait time and previously reported patient wait times; and displaying, using the application running on a plurality of other patient mobile devices communicating with the application server, the average wait time and other information about the provider on a provider's feed page in the application.

10. The system according to claim 9 further comprising inputting, by the patient using the application on the one mobile device, a rating of the provider and a comment about the provider.

11. The system according to claim 10 further comprising uploading the rating and the comment to the application server from the one mobile device, and displaying the final wait time, the rating and the comment on the provider's feed page in the application.

12. The system according to claim 9 further comprising stopping the timer to produce the final wait time, by the provider using a computing device communicating with the application server.

13. The system according to claim 9 further comprising entering an appointment time, by the patient using the application.

14. The system according to claim 13 further comprising downwardly revising the final wait time, by the application, if the timer was started before the appointment time.

15. The system according to claim 9 wherein displaying a running wait time for the patient includes displaying the running wait time, a current average wait time and a current maximum wait time as three concentric circular arcs centered around a start/stop button on a display of the one mobile device.

16. The system according to claim 9 wherein displaying the average wait time on a provider's feed page includes displaying the updated value of the average wait time calculated by the application server for non-subscribing providers, and displaying an office-reported wait time for subscribing providers.

17. A non-transitory computer readable medium storing instructions which, when executed, cause an application server and a plurality of mobile devices to perform steps including:

selecting a medical service provider, by a patient using a first mobile device running an application, where the first mobile device has Global Positioning System (GPS) capability and the first mobile device communicates with the application server;

using timer start and stop buttons and an upload button to measure and report a patient wait time at an office of the medical service provider, where the patient wait time is used by the application server to compute an aggregate average patient wait time which is displayed on a feed page of the medical service provider in the application;

initiating a patient procedure, by a medical technician using a second mobile device running the application, where the second mobile device is sterilizable and configured to remain with the patient during the procedure, where initiating a patient procedure includes defining a type of procedure, defining a specific operating room for the procedure, and establishing one or more message recipients for the patient procedure;

sending real-time status messages during the procedure, by the medical technician using the second mobile device, where the status messages are received by the one or more message recipients using the application on other mobile devices, where each of the mobile devices is in wireless communication with the application server using one or more of wireless local area networks, wireless broadband networks and cellular communication networks.

18. The non-transitory computer readable medium according to claim 17 wherein the real-time status messages are selectable from a pre-defined list of messages or typed in as custom messages using a keypad on the second mobile device, and the messages in the pre-defined list of messages are categorized by a phase of the procedure to which they are applicable.

* * * * *